United States Patent [19]

Zarling et al.

[11] Patent Number: 5,081,029
[45] Date of Patent: Jan. 14, 1992

[54] METHODS OF ADOPTIVE IMMUNOTHERAPY FOR TREATMENT OF AIDS

[75] Inventors: Joyce M. Zarling, Seattle; Shiu-Lok Hu, Redmond, both of Wash.

[73] Assignee: Oncogen, Seattle, Wash.

[21] Appl. No.: 304,926

[22] Filed: Feb. 1, 1989

Related U.S. Application Data

[63] Continuation of Ser. No. 909,447, Sep. 19, 1986, abandoned, which is a continuation-in-part of Ser. No. 779,909, Sep. 25, 1985, abandoned, which is a continuation-in-part of Ser. No. 842,984, Mar. 27, 1986, abandoned, and a continuation-in-part of Ser. No. 905,217, Sep. 9, 1986, abandoned.

[51] Int. Cl.$^5$ .................. C12P 21/00; C12N 15/00; C07H 15/12
[52] U.S. Cl. .................. 435/172.3; 435/235.1; 435/320.1; 435/240.2
[58] Field of Search .................. 435/68, 70, 91, 235, 435/317.1, 172.3, 320; 536/27; 935/1, 70, 32, 101

[56] References Cited

PUBLICATIONS

Smith et al., Nature 302: 490–495, 1983.
Chang et al., Science 228: 93–96, 1985,
Krowka et al., (1986) Abst. Communication 30:S3c International Conf. on AIDS, Jun. 23–25, Paris, France.
Koenig et al., (1986) Abst. Communication 25S3a, International Conf. on AIDS, Jun. 23–25, Paris, France.
Lotz et al. (1985) Journal Immunology, vol. 134, pp. 157–166.
Zarling et al. (1986) Journal Immunology, vol. 136, pp. 1469–1473.
Chang et al. (1985) Science, vol. 228, pp. 93–96.
Hu et al. (1986) Nature, vol. 320, pp. 337–340.
Rosenberg et al., European Patent Application Publication No. 211,769, 1987.
Zarling et al., 1986, J. Virol. 59: 506–509.
Cheever et al., 1986, J. Exp. Med. 163: 1100.
Zarling et al., 1986, J. Immunol. 136: 4669.
Koening et al., 1986, Abstract, Communication 26: ⅓a International Conference on AIDS.
Krowka et al., 1986, Abstract, Communication 38:53a.
Ledbetter et al., 1985, J. Immunol. 135: 2331–2336.
Rosenberg et al., 1986, N. Engl. J. Med. 313, 1485.
Rosenberg et al., 1985, J. Natl. Cancer Inst. 75: 595–603.
DeFreitas et al., 1985, Proc. Natl. Acad. Sci. U.S.A. 82: 3425–3429.
Lutze et al., 1985, J. Immunol. 134: 157–166.
Lukacher et al., 1984, J. Exp. Nep. Med. 160: 814–826.
Byrne and Oldstone, 1984, J. Virol. 51: 682–686.
Yasukawa and Zarling, 1984, J. Immunol. 133: 422–427.
Larson et al., 1984, J. Virol. 50: 56–59.
Masumbder and Rosenberg, 1984, J. Exp. Med. 159: 495–507.
Sethi et al., 1983, J. Gen. Virol. 64: 433–447.
Lawman et al., 1988, Inf. and Dmmun. 30: 451–461.
Sethi et al.: 1980, Nature (London) 286: 718–720.
Fernandez–Cruz et al., 1979, J. Immunol. 123: 1772–1777.
Biddison et al., 1979, J. Immunol. 122: 660–666.
McMichael and Askonas, 1978, Eur. J. Immunol. 8: 705–711.
Zweerink et al., 1977, Nature (London) 267: 354–356.
Institut Pasteur, PCT Application Publication No. WO 86/0283, 1986.
Levy et al., 1984, Science 225: 840–842.
Kalyanaraman et al., 1984, Science 225: 321–323.
Gallo et al., 1984, Science 224: 500–503.
Popovic et al., 1984, Science 224: 497–500.
Klatzman et al., 1984, Nature 312: 7670768.
Dalgleish et al., 1984, Nature 312: 763–766.
Peorino et al., 1984, Science 224: 69–72.
Barre-Sinoussi et al., 1983, Science 220: 868–871.
Weiss et al., (eds.), 1982, RNA Tumor Viruses, Cold Spring Harbor Laboratory, New York, pp. 226–227, 236.
Masur et al., 1981, N. Engl. J. Med. 305: 1431–1438.
Gottlieb et al., 1981, N. Engl. J. Med. 305: 1425–1431.
Tooze (ed.), 1973, The Molecular Biology of Tumor Viruses Cold Spring Laboratory, New York, pp. 534–535.
Plata et al., Abstracts, Communication 161: 527, International Conference on AIDS, Jun. 23–25, 1986.
Matia et al., 1984, J. Immunol. 135: 703–713.
Flyer et al., 1983, Nature (London) 305: 815–818.
Mitsuya et al., 1983, J. Exp. Med. 158: 994–995.
McMichael et al., 1986, J. Gen. Virol. 67: 719–726.
Blancou et al., 1986, Nature (London) 322: 373–375.
Cremer et al., 1985, Science 228: 737–740.
Yewdell et al., 1985, Proc. Natl. Acad. Sci., U.S.A. 82: 1785–1789.
Bennick et al., 1984, Nature (London) 322: 5: 578–580.
Smith et al., 1983, Proc. Natl. Acad. Sci. U.S.A. 80: 7155–7159.

(List continued on next page.)

Primary Examiner—Robin L. Teskin
Assistant Examiner—Beth A. Burrous
Attorney, Agent, or Firm—Pennie & Edmonds

[57] ABSTRACT

Immunotherapeutic methods for the treatment of patients infected with the AIDS virus are described. T lymphocytes which are histocompatible with the patient and specific for the AIDS virus are activated in vitro by exposure to AIDS virus-related epitopes. Activated T lymphocytes are expanded and inoculated into the patient in order to transfer T cell immunity directed against the AIDS virus epitopes.

17 Claims, No Drawings

OTHER PUBLICATIONS

Connor, S., 1986, New Scientist, Jul. 3, 1986, pp. 28–29.

Ciancolo et al., Inhibition of Lymphocyte Proliferation by a Synthetic Peptide Homologous to Retroviral Envelope Proteins, 1985, Science 230: 453–455.

Ciancolo et al., Inhibition of Lymphocyte Proliferation by a Synthetic Peptide Homologous to Envelope Proteins of Human and Animal Retrovirus, 98th Annual Meeting of Association of American Physicians, May 1985, Clin. Res. 33, 609A.

Harris et al., Inhibition of Natural Killer Cell Activity by a Synthetic Peptide Homologous to a Conserved Region in the Retroviral Protein, p. 15E, J. Immunol. 183(3): 889–894.

WO87/02038 (ONCOGEN) published Apr. 9, 1987 (EP Category: X, P).

GB2, 181,435A (ONCOGEN) published Apr. 23, 1987 (EP Category: X, P).

Zarling et al., Sep. 25, 1986, Nature 323:344–346 (EP Category: X, P).

FR-A-2 593,189 (Montagnier) Jul. 24, 1987 (EP Category: P, A).

FR-A-2 593,190 (Montagnier) Jul. 24, 1987 (EP Category: P, A).

WO86/02383 (Inst. Pasteur) Apr. 24, 1986 (EP Category: A).

EPO 211,769A (Rosenberg) Feb. 25, 1987 (EP Category: P, A).

METHODS OF ADOPTIVE IMMUNOTHERAPY FOR TREATMENT OF AIDS

This invention was made with Government support under Research Grant No. AI-28065 awarded by the National Institutes of Health. The government has certain rights in this invention.

This is a continuation, of application Ser. No. 909,447, filed Sept. 19, 1986 which is a continuation in part of the following copending United States applications which are incorporated by reference herein: Ser. No. 779,909 filed Sept. 25, 1985, now abandoned; Ser. No. 842,984, filed Mar. 27, 1986 now abandoned; and Ser. No. 905,217, filed Sept. 9, 1986 now abandoned.

Field of the Invention
Background of the Invention
    AIDS Virus
    Cell-Mediated Immunity to Retroviral Antigens
    In Vitro Activation of T Cells Directed Against Viruses
    Studies with Recombinant Vaccinia Viruses
Summary of the Invention
Detailed Description of the Invention
    Isolation, Activation, and Expansion of Lymphocytes
    Demonstration of Specific Cell-Mediated Immunity to AIDS Virus Related Epitopes
    Inoculation of Activated T Cells into the Patient
Example: In Vitro Activation of Macaque T Cells Specific to LAV/HTLV III
    Periperal Blood Lymphocytes from Vaccinated Macaques Proliferate in Response to Stimulation with LAV/HTLV III.
    Peripheral Blood Lymphocytes Activated by v-env5 or LAV/HTLV III are T Cells
    T Cells From Vaccinated Macaques Produce IL-2 Following Stimulation with LAV/HTLV III or v-env5
Example: In Vitro Activation of Chimpanzee T Cells Specific to LAV/HTLV III
Example: In Vitro Generation of Chimpanzee T Cell Clones With Proliferative and Cytotoxic Activities Directed Against LAV/HTLV III Envelope Antigens
Example: In Vitro Activation of Human T Cells With V-env 5

FIELD OF THE INVENTION

The present invention is directed to methods of adoptive immunotherapy in the treatment of patients infected with AIDS virus which involve in vitro activation of T cells that mediate an immune response against the AIDS virus, expansion of these T cells which are then inoculated into patients so that a cell-mediated immune response specifically directed against AIDS virus infected cells is transferred to the patient. The present invention provides for the isolation, in vitro activation, demonstration of immune specificity, expansion and administration of activated lymphocytes, which can be used to mediate an in vivo T-cell immune response to AIDS virus antigens. The method of the present invention comprises the isolation of lymphocytes from the patient or a histocompatible donor whose immune system has been exposed to AIDS virus antigen(s) and the in vitro activation of the lymphocytes by exposure to AIDS virus-related epitopes. Expansion of the T lymphocytes reactive to AIDS virus antigens, and inoculation of the T cells into patients suffering from AIDS virus-related disorders should prove a valuable form of immunotherapy.

BACKGROUND OF THE INVENTION

AIDS VIRUS

Acquired Immunodeficiency Syndrome (AIDS) is a disease characterized by severe immune deficiency due primarily to impairment of the patient's cell mediated immune response (Gottlieb, M., et al., 1981, N. Engl. J. Med. 305:1425; Masur, J., et. al., 1981, N. Engl. J. Med. 305:1431). Two clinical presentations of the disease are recognized: (a) a prodromal phase called Lymphadenopathy Syndrome (LAS) characterized by chronic lymphadenopathy, leukopenia and a quantitative decrease in peripheral blood helper cells (OKT4 cells) leading to a reversal of the normal peripheral helper to suppressor T lymphocyte ratio (OKT4:OKT8) which shifts from 2 to 0.1 or less as the disease progresses; and (b) an immuno-deficient state termed AIDS characterized by a decrease in OKT4 cells and reversal of the normal OKT4:OKT8 ratio, absolute lymphopenia, and repetitive opportunistic infections mainly by *Pneumocystis carnii;* this latter phase is ultimately associated with death in the majority of cases. Certain subsets of patients have increased incidence of lymphoma and Kaposi's sarcoma. Currently, there is no cure for the disease.

Epidemiological data along with information concerning the types of patients that acquired the disease suggested that an infectious agent transmitted by intimate contact might be the cause of the disease. Subsequently three groups have provided strong evidence that the causative agent of AIDS is a retrovirus with a tropism for helper T lymphocytes. These groups are:

(a) R. C. Gallo and coworkers at the National Institute of Health were able to isolate a cytopathic retrovirus (HTLV III) from patients with AIDS and pre-AIDS (Gallo, R. C., et al., 1984, Science 224:500; Popovic, M., et al., 1984, Science 224:497). They also detected antibodies against HTLV III in the serum of patients with AIDS.

(b) L. Montagnier and coworkers at the Pasteur Institute isolated a T-lymphotropic retrovirus (LAV) from a patient who presented with cervical lymphadenopathy and was at risk for AIDS (Barre-Sinoussi, F., et al., 1983, Science 220:868). This group was also able to demostrate antibodies against LAV in serum from AIDS patients (Kalysansraman, V. S., et al., 1984, Science 225:321). Moreover, they were able to isolate LAV from the lymphocytes of a patient who developed AIDS after receiving blood from a donor who developed AIDS (Feorino, P. M., et al., 1984, Science 225:69).

(c) J. Levy and coworkers isolated infectious retroviruses (termed AIDS-associated retrovirus, or ARV) from the peripheral mononuclear cells of patients with AIDS (Levy, J. A., et al., 1984, Science 225:840).

Although all three viruses were isolated independently, they all probably belong to the same retrovirus subgroup (Levy, J. A., et al., 1984, Science 225:840) and will be collectively referred to herein as LAV/HTLV III.

The general structure of retroviruses is that of a ribonucleoprotein core surrounded by a lipid containing envelope which the virus acquires during the course of cell budding. Embedded within the envelope and projecting outward are the viral encoded glycoproteins. These determine the host range of the virus and react with specific receptors on the surface of susceptible cells. Neutralizing antibodies are thought to bind to envelope glycoproteins and block their interaction with receptors on the surface of cells (pp. 534-535 in, The Molecular Biology of Tumor Viruses, ed. John Tooze, 1973, Cold Spring Harbor Laboratory; pp. 226-227 and 236-237 in, RNA Tumor Viruses, ed. R. Weiss, N. Teich, H. Varmus, and J. Coffin, 1982, Cold Spring Harbor Laboratory.). In the specific case of LAV/HTLV III, there is evidence that the $T_4$ antigen, present on a subset of T-lymphocytes, is the receptor or a component of the receptor for the virus (Dalgleish, A. G., et al., 984, Nature 312:763; Klatzmann, D., et al., 1984, Nature 12:767).

The RNA genome of LAV/HTLV III contains the gag gene, which codes for the internal structural proteins (core proteins) of the virus and defines the viral group-specific antigens, the pol gene, which codes for the virion associated reverse transcriptase, and the env gene, which codes for the viral glycoproteins. Other regions such as sor and 3'-orf denote areas of the genome containing open reading frames; the function of these regions is not known at present.

CELL-MEDIATED IMMUNITY TO RETROVIRAL ANTIGENS

Little is known concerning antigenic specificity of T cells to retroviruses. However, an envelope glycoprotein, gp70, of Friend and Moloney murine leukemia virus (MuLV) has been reported to be recognized by MuLV immune mouse T cells (Matis, L. A., et al., 1985, J. Immunol. 135:703-713; Flyer, D. C., et al., 1983, Nature 305:815-818). Plata et al. (Abstract, Communication 161:527k, International Conference on AIDS, June 23-25, 1986, Paris, France) have shown that mice can generate cytotoxic T cells to envelope or gag antigens expressed on transfected MuLV-induced tumors. T lymphocytes directed against cells infected with human T lymphotropic virus type I (HTLV-I) have been demonstrated (Mitsuya, H., et al., 1983, J. Exp. Med. 158:994-999), but the antigens that are recognized have not been reported.

IN VITRO ACTIVATION OF T CELLS DIRECTED AGAINST VIRUSES

T cell-mediated immunity, in addition to antibodies, has been shown to play an important role in resistance to, or recovery from, diseases caused by many different enveloped viruses. There have been several studies showing that T lymphocytes, capable of specifically recognizing virus-infected cells, can be generated in vitro by stimulating the lymphocytes from virus-infected or immunized animals with viruses, viral proteins, or viral peptides. In the mouse, examples include T lymphocytes that specifically recognize cells infected with influenza virus (Zweerink, H. J., et al., 1980, Nature 267:351), herpes simplex virus (HSV) (Lawman, M. J. P., et al., 1980, Infec. Immun. 30:451), or murine leukemia/sarcoma viruses (Fernandez-Cruz, E., et al., 1979, J. Immunol. 123:1772). Such sensitized T cells have been shown to have either cytotoxic activity (and are referred to as cytotoxic T lymphocytes, CTL) and/or T helper cell activity measured by the ability of the T cells to proliferate and produce lymphokines in response to stimulation with virus or viral antigens. Evidence that such in vitro activated T cells may be of immunotherapeutic value when inoculated into experimental animals is based on findings that virus activated mouse T cells or T cell clones can adoptively transfer resistance to disease or death caused by such viruses as influenza (Lukacher, A. E., et al., 1984, J. Exp. Med. 160:814), lymphocytic choriomeningitis virus (Byrne, J. A. and Oldstone, M. B. A., 1984, J. Virol. 51:682), herpes simplex virus (HSV) (Larsen, H. L., et al., 1984, J. Virol. 50:56; Sethi, K. K., et al., 1983, J. Virol. 64:443) or murine leukemia virus (Cheever, M. A., et al., 1986, J. Exp. Med. 163:1100). In addition, mouse lymphocytes, non-specifically activated with interleukin 2 (IL-2) and referred to as lymphokine activated killer (LAK) cells have been shown to be of immunotherapeutic value in eliminating metastases from a variety of mouse tumors (Rosenberg, S. A., 1985, J. Natl. Cancer Dist. 75:595; Mazumder, A. and Rosenberg, 1984, J. Exp. Med. 159:225).

It has also been possible to activate T helper and/or cytotoxic T cells from humans by stimulating peripheral blood lymphocytes (PBL) with viruses or viral antigens. For example, human T cells specifically recognizing HSV (Sethi, K. K., et al., 1980, Nature 270:529; Yasukawa, M. and Zarling, J., 1984, J. Immunol. 133:422) or influenza virus (Biddison, E. W., et al., 1981, J. Immunol. 122:660; McMichael, A. J. and Askonas, B. A., 1979, Eur. J. Immunol. 5:705) have been generated in vitro. In the HSV system, purified HSV, HSV glycoproteins cloned and expressed in mammalian cells, and particular HSV peptides have been reported to activate HSV specific human T cells (Zarling, J. M., et al., 1986, J. Immunol. 136:4669; DeFreitas, E. C., et al., 1985, Proc. Natl. Acad. Sci. U.S.A. 82:3425). Although the use of in vitro-sensitized virus-specific human T cells has not been reported, it has recently been reported that human LAK cells, after inoculation into cancer patients together with IL-2, can cause regression of a variety of tumors (Rosenberg, S. A., et al., 1985, N. Engl. J. Med. 313:1485). However, LAK cells can also cause side effects similar to those associated with graft versus host disease. These side effects may be partially accounted for by recent observations that normal lymphocytes, in addition to cancer cells, can be killed by LAK cells (Sondel, P. M., et al., 1985, Science 228:1785).

STUDIES WITH RECOMBINANT VACCINIA VIRUSES

Recombinant vaccinia viruses expressing antigens of foreign viruses have been found to induce resistance to challenge with the foreign viruses in experimental animals. Examples include recombinant vaccinia viruses expressing an HSV glycoprotein (Cremer, K. J., et al., 1985, Science 228:1985), a rabies virus surface antigen (Blancou, J., et al., 1986, Nature 322:373), and an influenza virus nucleoprotein (Smith, G. L., et al., 1983, Proc. Natl. Acad. Sci. U.S.A. 80:7155; Yewdell, J. W., et al., 1985, Proc. Natl. Acad. Sci. U.S.A. 82:1785). The recombinant vaccinia virus expressing influenza virus nucleoprotein has been reported to induce specific T cell-mediated immunity to influenza virus in immunized mice (Bennink, J. R., et al., 1984, Nature 311:578). In addition, using target cells infected with a recombinant vaccinia virus expressing influenza virus nucleoprotein, it has been demonstrated that influenza virus nucleoprotein is recognized by cytotoxic T cells from influenza seropositive donors (McMichael, A. J., et al., 1986, J. Gen. Virol. 67:719). Similarly, we have recently found that human target cells infected with a recombinant vaccinia virus expressing an HSV glycoprotein, are recognized by human CTL clones specific for HSV (Zarling, J. M., et al., 1986, J.Virol. 59:506). We have also been able to generate human T cell clones specific for HSV-infected cells by stimulating PBL from humans who have been infected with HSV, with a recombinant vaccinia virus that expresses an HSV glycoprotein (Zarling et al., J. Virol, supra).

SUMMARY OF THE INVENTION

The present invention is directed to methods which utilize in vitro activation of T lymphocytes in adoptive immunotherapy of AIDS virus-related disorders. The lymphocytes of the invention can be isolated from any individual(s) whose immune systems has been exposed to AIDS virus antigens including but not limited to the AIDS or AIDS-related complex (ARC) patient himself, and HLA-compatible donors immunized by natural exposure to the AIDS virus or by vaccination with AIDS virus-related epitopes. The lymphocytes are stimulated in vitro by exposure to any peptide or protein related to an epitope(s) of AIDS virus. These epitopes can be contained in any composition including recombinant vectors such as viruses, or in purified proteins or peptides, whether natural, recombinant, or synthetic.

The invention provides for the demonstration of reactivity to AIDS virus epitopes by the activated T lymphocytes, and expansion of the activated lymphocytes in cell culture, before inoculation into the patient. Inoculation of the patient with AIDS virus-reactive T cells, may or may not be accompanied by other therapeutic regimens such as administration of IL-2, interferon, anti-LAV/HTLV III antibodies, antiviral drugs, bone marrow transplants, etc.

Very recently, the lysis of LAV/HTLV III infected lymphocytes by cytotoxic T cells (CTL) and lymphokine-activated killer (LAK) cells has been described (Koenig, S., et al., Abstract, Communication 26:§3a, International Conference on AIDS, June 23-25, 1986, Paris, France). Evidence was found for the existence of cells cytotoxic for LAV/HTLV III infected targets in AIDS virus-seropositive individuals. In addition, Krowka et al. (Abstract, Communication 30:S3e, International Conference on AIDS, June 23-25, 1986, Paris, France) has provided evidence that some AIDS virus-seropositive donors' peripheral blood lymphocytes proliferate and/or release IL-2 in response to recombinant AIDS virus antigens.

An advantage of the use of AIDS virus specific T cells for immunotherapy of AIDS virus infections in accordance with the present invention would be that these T cells should recognize virus infected, but not normal, cells. Recent advances in the technologies for large scale culture of mammalian cells (Feder, J. and Tolbert, W., 1983, Sci. American 248:36; Altschuller, G. L., et al., 1986, Biotech. and Bioengineering 28:646), including the continuous growth of human T cells in IL-2, enables testing of an adoptive immunotherapeutic approach for treating individuals infected with AIDS virus.

In specific embodiments of the present invention, lymphocytes isolated from macaques and chimpanzees, immunized with a recombinant virus expressing AIDS virus envelope determinants, as well as human lymphocytes obtained from patients who are seropositive for the AIDS virus were induced to proliferate in vitro upon exposure to AIDS virus envelope epitopes and/or a recombinant vaccinia viruses expressing AIDS virus envelope epitopes. The stimulated macaque lymphocytes were shown to be T cells, which produce IL-2 following stimulation. Furthermore, T cells of helper or cytotoxic activity were generated in chimpanzees.

DETAILED DESCRIPTION OF THE INVENTION

The present invention is directed to methods for immunotherapeutic treatment of patients infected with AIDS virus, comprising the in vitro activation of lymphocytes with AIDS virus-related epitope(s) prior to inoculation into patients. The activated T cells are expanded in cell culture and inoculated into patients infected with the AIDS virus, as a form of adoptive immunotherapy, alone or in conjunction with other therapeutic regimens. Methods are described for activating peripheral blood lymphocytes (PBL) so that they can specifically recognize AIDS virus infected cells and can contribute to the elimination of the virus or virus-infected cells, but not normal cells. Such activated PBL can mediate their effect either by directly killing virus infected cells or by producing lymphokines that can inhibit production of infectious virus and/or can activate other cells to kill the virus infected cells.

The method of the invention may be divided into the following stages solely for the purpose of description: (a) isolation, in vitro activation, and expansion of T lymphocytes, (b) demonstration of induction of specific cell-mediated immunity, and (c) inoculation of activated T cells into the patient.

For clarity of discussion, the method will be discussed mainly in terms of using recombinant vaccinia viruses expressing AIDS virus envelope glycoproteins. The same method, however, may be applied in an analogous fashion for the use of other recombinant viruses expressing different AIDS virus-related epitopes such as gag proteins, or for the use of peptides or proteins produced by other recombinant DNA technologies or by chemical synthesis, or purified from virions, patients blood or serum, etc.

ISOLATION, ACTIVATION, AND EXPANSION OF LYMPHOCYTES

Lymphocytes used for in vitro activation are T lymphocytes directed against AIDS virus epitopes. These T cells can be obtained by isolating peripheral blood lymphocytes (PBL) from individuals who have been exposed to AIDS virus-related epitopes and who are compatible for human leukocyte antigen(s) (HLA). Such suitable individuals include the patient himself (who may have AIDS or AIDS-related complex, ARC) or a HLA-matched donor who has been exposed to the AIDS virus-related epitopes by natural exposure to AIDS virus or by vaccination with AIDS virus-related epitopes.

The present invention is directed to the use of peptides or proteins related to an epitope(s) of AIDS virus in the in vitro stimulation of T lymphocytes. These peptides or proteins include naturally occurring molecules which can be purified by various techniques known in the art from AIDS virus virions, patient blood, serum, etc. For example, LAV/HTLV III envelope glycoproteins can be purified from disrupted LAV/HTLV III by lentil lectin chromatography. Other possible methods of purification include but are not limited to other types of chromatography (e.g., ion-exchange, affinity, sizing column), centrifugation, differential solubility, immunoprecipitation and preparative gel electrophoresis, or by any other standard technique for the purification of proteins. The peptides or proteins used for stimulation can also be purified from recombinant viruses or any other products of recombinant DNA technology. The peptides or proteins related to AIDS virus epitope(s) for use in this invention can be produced in and isolated from any host cell-expression vector system; these include, for example, animal or insect cell cultures infected with appropriate recombinant virus; microorganisms such as bacteria transfected with recombinant plasmids, cosmids or phage; and yeast transformed with recombinant plasmids. In addition, the recombinant microorganism itself, containing the AIDS virus-related epitopes, may be used. These microorganisms should contain the epitope so that it is exposed to the T lymphocytes, either in its usual state, or following antigen processing by other cells such as macrophages, or by treatment (for example with denaturing agents, detergents, etc.) so that the AIDS virus-related epitope is uncovered. Alternatively, peptides and proteins containing AIDS virus-related epitopes can be chemically synthesized and used for stimulating the lymphocytes. Examples of AIDS virus-related epitopes which may be used in accordance with the present invention include, but are not limited to those disclosed in copending U.S. application Ser. No. 779,909 filed Sept. 25, 1985, Ser. No. 842,984, filed Mar. 27, 1986 and U.S. application corresponding to Ser. No. 905,217, filed Sept. 9, 1986 which are incorporated by reference herein.

Various methods known in the art of enhancing the proliferation of the stimulated T cells may be used, and are within the scope of the invention. For example, antibodies or their derivative molecules which recognize the Tp67 or Tp44 antigens on T cells have been shown to augment proliferation of activated T cells (Ledbetter, J. A., et al., 1985, J. Immunol. 135: 2331), and may be used during in vitro activation to increase proliferation. Interferon has been found to augment the generation of cytotoxic T cells (Zarling et al., 1978, Immunol. 121:2002), and may be used during in vitro activation to augment the generation of cytotoxic T cells against AIDS virus infected cells.

The activated T cells can then be expanded in cell culture. This expansion can be accomplished by repeated stimulation of the T cells with AIDS virus related epitopes with or without IL-2 or by growth in medium containing IL-2 alone. Other methods of T cell cultivation (for example with other lymphokines, growth factors, or other bioactive molecules) are also within the scope of the invention. The use of antibodies or antibody fragments which define T cell antigens such as the Tp67 or Tp44 antigens which can aid in the growth and maintenance of T cells in vitro, (Ledbetter, J. A.., et al., 1985, J. Immunol. 135: 2331) is also within the scope of the invention.

The description infra details a general method for isolation, activation, and expansion of PBL, mainly in terms of using recombinant vaccinia viruses containing AIDS virus envelope epitopes. However the present invention provides for the use of any AIDS virus-related epitopes in various forms, as described supra, and modifications and adaptations to the method to accomodate these variations as well as different procedures known in the art are within the scope of the invention.

Approximately 200 ml of heparinized venous blood is drawn by venipuncture and PBL are isolated by Ficoll-hypaque gradient centrifugation, yielding approximately 1 to $5 \times 10^8$ PBL, depending upon the lymphocyte count of the donors. The PBL are washed in phosphate-buffered saline and are suspended at approximately $2 \times 10^5$/ml in RPMI 1640 medium containing 10% pooled heat-inactivated normal human serum from AIDS seronegative donors; this medium will be referred to as "complete medium." The cells are placed in 750 ml tissue culture flasks to which is added either ultraviolet (UV) light-inactivated recombinant virus that expresses an AIDS virus epitope, such as a recombinant vaccinia virus which expresses an AIDS epitope ($1 \times 10^6$ to $1 \times 10^7$ plaque forming units/ml prior to UV light inactivation) or proteins or peptides related to an AIDS-virus epitope generally ranging from 1–10 ug/ml). Six to seven days later, the lymphocytes are restimulated using the same concentration of recombinant virus, proteins or peptides. Three days later the cells are centrifuged and resuspended in fresh complete medium to which is added endotoxin-free recombinant human IL-2 (approximately 100 units IL-2 per ml). The cells are then seeded in roller bottles at approximately $2 \times 10^5$ cells/ml, and the roller bottles are continuously rotated at 0.5 to 1 revolution per minute. The cells are reseeded at $2 \times 10^5$ cells/ml when they reach a density of approximately $1 \times 10^6$/ml. Alternatively, approximately 1 to $3 \times 10^8$ cells in complete medium with IL-2 are seeded in a hollow fiber cell culture system such as the Acusyst P (Endotronics, Coon Rapids, Minnesota) in which the lymphocytes are continuously bathed in fresh medium with IL-2.

When the total number of cells in roller bottles or the hollow fiber cell culture system reaches approximately $1 \times 10^{10}$ cells, they are centrifuged in conical bottles and the pellets washed twice with Hanks' Balanced Salt Solution without calcium, magnesium, or phenol red. The cells are then resuspended in infusion medium consisting of 200 ml of 0.9% sodium chloride containing 5% normal human serum albumin and 75,000 units of recombinant human IL-2. The cell suspension is then filtered through sterile 110 mesh and put into Fenwall transfer packs. Samples of the cells are tested for the presence of microorganisms including fungi, aerobic and anaerobic bacteria, and mycoplasma. A sample of the cells is retained for immunological testing, as described infra, in order to demonstrate induction of specific immunity.

DEMONSTRATION OF SPECIFIC CELL-MEDIATED IMMUNITY TO AIDS VIRUS RELATED EPITOPES

Before use in immunotherapy, the stimulated lymphocytes are tested for cell-mediated immune reactivity against AIDS virus-infected cells. The PBL, following stimulation with recombinant vectors expressing AIDS virus-related epitope(s) or with proteins or peptides containing such epitope(s), can be examined with regard to cell surface expression of T and B cell markers by immunofluorescent analysis using fluorescein-conjugated monoclonal antibodies to T and B cell antigens. An example of such an assay is described infra, in Section 5.2. Expression of known T cell markers, such as the CD4 and CD8 antigens, confirms the identity of the activated lymphocytes as T cells.

The activated T cells are then tested for reactivity against AIDS virus epitopes. This could be accomplished by any of several techniques known in the art for assaying specific cell-mediated immunity. For example, a cytotoxicity assay, which measures the ability of the stimulated T cells to kill the patient's autologous AIDS virus-infected cells in vitro, may be accomplished by incubating the lymphocytes with $^{51}$Cr-labelled cells, such as phytohemagglutinin activated T cells, infected with LAV/HTLV III, recombinant vaccinia viruses expressing AIDS related epitopes, parental vaccinia virus, and uninfected labelled cells, and measuring $^{51}$Cr release upon lysis. Such assays have been described (see, for example, Zarling, J. M., et al., 1986, J. Immunol. 136:4669). The activated PBL could also be tested for T helper cell activity by measuring their ability to proliferate, as shown by $^3$H-thymidine incorporation, following stimulation, and/or by measuring their ability to produce lymphokines such as IL-2 or interferon upon stimulation, in the absence of exogenous IL-2. Examples of such assays are described in the specific embodiment of the invention, infra, in Sections 5.1, 5.3, 6, and 7. Other assays of specific cell-mediated immunity known in the art, such as leukocyte-adherence inhibition assays (Thomson, D. M. P. (ed.), 1982, Assessment of Immune Status by the Leukocyte Adherence Inhibition Test, Academic Press, New York), may also be used.

INOCULATION OF ACTIVATED T CELLS INTO THE PATIENT

The procedure detailed infra is a generalized description of part of the method of the invention. Modifications and adaptations to accommodate different procedures known in the art are within the scope of the present invention.

Inoculation of the activated T cells is preferably through systemic administration. The T cells can be administered intravenously through a central venous catheter or into a large peripheral vein. Other methods of administration (for example, direct infusion into an artery) are within the scope of the invention. Approximately $1 \times 10^8$ cells are infused initially and the remainder are infused over the following several hours. In some patients, recombinant human IL-2 may be used and will be infused intravenously every 8 hours beginning at the time of T cell infusion. Injections of IL-2 will preferably be at doses of 10,000 to 100,000 units/kg bodyweight, as previously used in cancer patients (Rosenberg, S. A., et al., 1985, N. Engl. J. Med. 313:1485). The IL-2 infusion will be continued for several days after infusion of the activated T cells if tolerated by the patient.

Treatment by inoculation of activated T cells can be used alone or in conjunction with other therapeutic regimens including but not limited to administration of IL-2 (as described supra), interferon, drugs that inhibit AIDS virus replication, or monoclonal antibodies to the AIDS virus, or bone marrow transplants from healthy HLA matched donors.

The patient can be monitored for evidence of elimination of mononuclear lymphocytes expressing viral antigens in the blood and lymph nodes and can be followed for long term clinical effects on lymphadenopathy, the development of opportunistic infections, Kaposi's sarcoma, and other ARC and AIDS-associated disorders.

In the examples that follow, the in vitro activation of T cells was demonstrated using PBL obtained from humans exposed to the AIDS virus or nonhuman primates immunized with the compositions more completely described in the copending parent applications: Ser. No. 779,909 filed Sept. 25, 1985; Ser. No. 842,984 filed Mar. 27, 1986; and U.S. application corresponding to Ser. No. 905,217, filed Sept. 9, 1986 which are incorporated by reference herein.

EXAMPLE: IN VITRO ACTIVATION OF MACAQUE T CELLS SPECIFIC TO LAV/HTLV III

In this particular embodiment of the invention, we describe the in vitro activation of T cells specific to LAV/HTLV III, in Macaca fasicularis (macaques) immunized with a recombinant virus expressing the envelope glycoproteins of LAV/HTLV III.

PERIPHERAL BLOOD LYMPHOCYTES FROM VACCINATED MACAQUES PROLIFERATE IN RESPONSE TO STIMULATION WITH LAV/HTLV III

Eight macaques were immunized with a recombinant vaccinia virus that expresses the envelope glycoproteins gp41 and gp110 of LAV/HTLV III (v-env5), or a vaccinia recombinant virus expressing herpes simplex virus glycoprotein D-1 (v-HSVgD1); both of the recombinant viruses were constructed with the WR strain of vaccinia virus. Immunization was accomplished intradermally, by local scarification on the midline of the back, with $2 \times 10^7$ or $2 \times 10^8$ pfu (plaque forming units) of recombinant virus, followed by a second intradermal immunization of seven of the macaques 12 weeks later. Peripheral blood lymphocytes (PBL) were isolated by Ficoll-hypaque centrifugation from heparinized blood of the immunized macaques four weeks after the second immunization. PBL were also isolated from nonimmunized macaques, and from macaque 81, which was vaccinated only once with v-env5. The PBL were suspended in RPMI 1640 medium (GIBCO, Grand Isle, N.Y.) supplemented with 10% heat-inactivated normal human serum. $1 \times 10^5$ PBL, in a final volume of 0.1 ml medium, were placed into wells of round bottomed 96-well plates. To each well was added 0.1 ml medium containing ultraviolet (UV) light-inactivated v-env5 ($1 \times 10^6$ pfu/ml prior to UV-inactivation), or nondisrupted LAV/HTLV III (1 ug/ml, approximately $1 \times 10^5$ TCID$_{50}$, Tissue Culture Infective Dose$_{50}$) that has been purified by two cycles of sucrose gradient centrifugation from supernatants of LAV/HTLV III infected CEM cells, an HLA DR negative T cell leukemia line. Six days after stimulation, each well of PBL was labeled with 1 uCi $^3$H-TdR ($^3$H-thymidine, New England Nuclear, Boston, Mass.) for 6 hours, the cells were harvested and cpm $^3$H-TdR incorporated was determined by liquid scintillation counting. Results are shown in Table I. The values shown for cpm $^3$H-TdR incorporated are the mean values of four replicate wells. The stimulation index was calculated by dividing the cpm $^3$H-TdR incorporated into stimulated cells by the cpm incorporated into non-stimulated cells.

TABLE I

LAV/HTLV III INDUCED PROLIFERATIVE
RESPONSES OF PBL FROM MACAQUES AFTER
IMMUNIZATION WITH A VACCINIA RECOMBINANT
VIRUS EXPRESSING LAV/HTLV III ENVELOPE
GLYCOPROTEINS

| Macaque No. | Immuni- zation | Virus Used For PBL Stimulation | | | | |
|---|---|---|---|---|---|---|
| | | None | LAV/HTLV III | | V-env5 | |
| | | cpm* | cpm* | SI** | cpm* | SI** |
| 67 | v-env5 | 1,586 | 7,465 | 4.7 | 60,415 | 38.1 |
| 68 | v-env5 | 2,245 | 9,075 | 4.0 | 28,638 | 12.8 |
| 74 | v-env5 | 1,585 | 4,732 | 3.0 | 21,487 | 13.6 |
| 75 | v-env5 | 581 | 8,645 | 14.9 | 37,847 | 14.1 |
| 76 | v-env5 | 2,479 | 5,987 | 2.5 | 36,657 | 14.8 |
| 80 | v-env5 | 1,077 | 13,922 | 12.9 | 24,752 | 23.0 |
| 81 | v-env5 | 965 | 3,985 | 4.1 | 40,572 | 42.0 |
| 82 | v-env5 | 2,581 | 8,580 | 3.3 | 46,847 | 18.1 |
| 73 | V-HSVgD1 | 612 | 553 | 1.0- | 56,217 | 91.9 |
| 26 | none | 2,911 | 1,822 | 1.0- | 2,240 | 1.0- |
| 27 | none | 1,228 | 1,072 | 1.0- | 2,532 | 2.0 |

*cpm $^3$H-TdR incorporated
**Stimulation Index.

As shown in Table I, PBL from all 8 macaques immunized with v-env5 incorporated 2.5 to 14.9 fold more $^3$H-thymidine 6 days after stimulation with LAV/HTLV III than did non-stimulated PBL. PBL from all of these macaques and also from macaque 73, which was immunized with the v-HSVgD1 recombinant virus, incorporated 12.8 to 91.9 fold more $^3$H-thymidine than did non-stimulated PBL, following stimulation with v-env5 (Table I) or with parental vaccinia virus. However, PBL from non-immunized macaques 26 and 27 or from v-HSVgD1-immunized macaque 73 did not proliferate in response to stimulation with LAV/HTLV III on day 6 (Table I) or on days 5 or 7 following stimulation with any of several concentrations of LAV/HTLV III. Thus, immunization with v-env5 specifically induces T cells which proliferate in response to LAV/HTLV III.

PERIPHERAL BLOOD LYMPHOCYTES ACTIVATED BY V-ENV5 OR LAV/HTLV III ARE T CELLS

In order to confirm that the PBL activated by v-env5 or LAV/HTLV III comprise T lymphocytes, PBL from vaccinated macaques, stimulated for 6 days with LAV/HTLV III or v-env5, were examined by two color immunofluorescence for expression of IL-2 receptors (that are present on activated T cells and activated B cells), CD4 and CD8 antigens (present on T cells), and CD20 (Bp35) antigen (present on B cells). This was accomplished by the following procedure:

PBL isolated from macaques 74 and 80, following immunization and boosting with the recombinant vaccinia virus v-env5, were cultured in medium alone or were stimulated for 6 days with v-env5 or LAV/HTLV III as described in Section 5.1 supra. The PBL were then examined by two color immunofluorescence for expression of interleukin-2 receptors (IL-2R), T cell associated CD4 and CD8 antigens, and B cell associated CD20 (Bp35) antigen using monoclonal antibodies previously found to react with macaque PBL (Clark, E. A., et al., 1983, Immunogenetics 18:599–615). The PBL were stained simultaneously with phycoerythrin-conjugated monoclonal antibody 2A3 (Becton-Dickinson, Inc., Mountain View, Calif.) to the interleukin-2 receptor (IL-2R) and fluorescein-conjugated monoclonal antibodies 1F5 (Clark, E. A., et al., 1985, Proc. Natl. Acad. Sci. U.S.A. 82:1766–1770) (Genetic Systems Corp., Seattle, Wash.) to CD20, G10-1 (Ledbetter, J. A., et al., 1985, J. Immunol. 134:4250–4254) (Genetic Systems Corp., Seattle, Wash.) to CD8, or T4$_a$ (Ortho Diagnostics, Raritan, N.J.) to CD4. The antibodies were used at saturating concentrations as previously determined by titrations on lymphocytes analyzed by flow microfluorometry with a modified FACS IV sorter (Becton-Dickinson, Mountain View, Calif.). Quantitative two color analysis was performed as previously detailed (Ledbetter, J. A., et al., 1984, in Perspectives in Immunogenetics and Histocompatibility, Vol. 6, Lymphocyte Surface Antigens (ed. E. Heidl), American Society of Histocompatibility and Immunogenetics, New York, pp. 119–129). The forward and right angle scatter gates were set to include lymphoblasts and a substantial number of small lymphocytes. The results are shown in Table II, in which the values listed are those for the total percent IL-2R+ cells and for the percent IL-2R+ cells coexpressing CD4, CD8 or CD20 (Bp35).

TABLE II

EXPRESSION OF IL-2 RECEPTORS AND CD4, CD8 OR
CD20 (BP35) ANTIGENS ON PBL FROM VACCINATED
MACAQUES AFTER STIMULATION WITH
LAV/HTLV III OR A RECOMBINANT VACCINIA
VIRUS EXPRESSING LAV/HTLV III ENVELOPE
GLYCOPROTEINS (V-ENV5)

| Macaque No. | PBL Stimulated With | Total % IL-2R+ Cells | % IL-2R+ Cells Coexpressing | | |
|---|---|---|---|---|---|
| | | | CD4 | CD8 | CD20 (Bp35) |
| 74 | v-env5 | 27.7 | 48.6 | 52.2 | 2.0 |
| 80 | v-env5 | 25.6 | 62.4 | 40.0 | NT |
| 74 | LAV/HTLV III | 14.7 | 50.0 | 59.0 | 1.9 |
| 80 | LAV/HTLV III | 12.0 | 58.0 | 38.0 | 1.5 |
| 80 | no virus | 0.3 | 0.3- | 0.3- | 0.3- |

The results in Table II show that nearly all of the virus-stimulated PBL that express IL-2 receptors coexpress CD4 or CD8 antigens, whereas only 1.5 to 2% coexpress CD20 (Bp35) antigen, indicating that v-env5 or LAV/HTLV III activated PBL are T cells.

T CELLS FROM VACCINATED MACAQUES PRODUCE IL-2 FOLLOWING STIMULATION WITH LAV/HTLVIII OR V-ENV5

T cells, following antigenic stimulation, produce lymphokines including IL-2 which can promote differentiation and/or proliferation of T and B cells, and can activate natural killer cells that can lyse cells infected with a variety of viruses including AIDS virus (Santoli, D., et al., 1978, J. Immunol. 121:526; Yasukawa, M., and Zarling, J. M., 1983, J. Immunol. 131:2011; Ruscetti, F. W., et al., 1986, J. Immunol. 136:3619). We therefore asked whether T cells from the vaccinated macaques produce IL-2 following stimulation with LAV/HTLV III.

PBL were isolated from heparinized blood of macaques four weeks following a second intradermal immunization with v-env5 or v-HSVgD1, both constructed with the WR strain of vaccinia virus (Exp. 1). For Experiment 2, PBL were isolated from macaques four weeks after a primary intradermal immunization with $2 \times 10^8$ pfu of v-env5, v-HSVgD1, or a v-env5 recombinant virus constructed with the New York City Board of Health vaccine strain of virus (v-env5NY). The PBL were suspended in RPMI 1640 medium supplemented with 10% heat-inactivated normal human serum, and $2 \times 10^5$ PBL were placed into wells of round bottomed 96-well plates followed by the addition of UV light-inactivated v-env5 ($1 \times 10^6$ pfu/ml prior to UV light-inactivation) or purified LAV/HTLV III (1 ug/ml) to the wells. Two days after stimulation, supernatants were harvested from the replicate wells and were tested for their ability to support proliferation of IL-2 dependent CTLL-2 cells (provided by Dr. S. Gillis, Immunex Corp., Seattle, Wash.) that were washed free of IL-2 for 24 hours prior to the assay. During the last six hours of incubation with the supernatants, the cells were labeled with $^3$H-TdR and $^3$H-TdR incorporation into the cells was determined. The units of IL-2 activity present in the supernatants were calculated as described (Gillis, S., et al., 1978, J. Immunol. 120:2027) from standard curves obtained from testing the effect of recombinant human IL-2 (provided by Dr. Gillis) on proliferation of CTLL-2 cells. The results are shown in Table III.

TABLE III

IL-2 PRODUCTION BY PBL FROM VACCINATED MACAQUES AFTER STIMULATION WITH LAV/HTLV III OR RECOMBINANT VACCINIA VIRUSES EXPRESSING AIDS VIRUS ENVELOPE GLYCOPROTEIN

| Macaque No. | Immunization | IL-2 (units/ml) Supernatants of PBL Stimulated With | | |
|---|---|---|---|---|
| | | No Virus | LAV/HTLV III | v-env5 |
| Experiment 1: | | | | |
| 67 | v-env5 | 0 | 28.0 | 96.0 |
| 68 | v-env5 | 0 | 16.0 | 124.0 |
| 74 | v-env5 | 0 | 9.0 | 52.0 |
| 73 | v-HSVgD1 | 0 | 0 | 108.0 |
| 26 | none | 0 | 0 | 0 |
| Experiment 2: | | | | |
| 03 | v-env5 | 0 | 14.4 | 55.8 |
| 05 | v-env5NY | 0 | 16.8 | 33.3 |
| 49 | v-env5NY | 0 | 7.1 | 26.7 |
| 52 | v-env5NY | 0 | 2.4 | 27.6 |
| 59 | v-HSVgD1 | 0 | 0 | 27.6 |
| 26 | none | 0 | 0 | 0 |
| 27 | none | 0 | 0 | 0 |

The results of Experiment 1 in Table III show that supernatants from v-env5 or LAV/HTLV III stimulated PBL, from macaques immunized twice with v-env5, contained IL-2 as shown by their ability to induce proliferation of CTLL-2 cells, an IL-2 dependent cell line. Similarly, as shown in experiment 2 of Table III, IL-2 was detected in supernatants of LAV/HTLV III or v-env5 stimulated PBL from macaque 03, which was immunized once with v-env5, and from all three macaques that were immunized once with a similar recombinant (v-env5NY) constructed using the New York City Department of Health strain of vaccinia virus that has been used as a smallpox vaccine in humans (Neff, J. M., 1985, in Vaccinia Viruses as Vectors for Vaccine Antigens (ed. G. V. Quinnan, Jr.), Elsevier, N.Y., pp. 69–76). In contrast, PBL from macaques 73 and 59, that were immunized with the vacciniaHSVgD1 recombinant virus, produced IL-2 following stimulation with v-env5 only, and not after stimulation with LAV/HTLV III (Table III). Non-immunized macaques 26 and 27 did not produce detectable IL-2 after stimulation with either LAV/HTLV III or v-env5. Since primarily T cells with helper/inducer activity produce IL-2 after antigenic stimulation (Moller, G. (ed.), 1980, Immunol. Rev., Vol. 51; Moretta, L., et al., 1982, Semin. Hematol. 19:273–284; Reinherz, E. L. and Schlossman, S. F., 1980, Cell 19: 821–827; Moretta, A., 1985, Eur. J. Immunol. 15: 148–155), these results thus demonstrate the presence of helper T cells, which recognize LAV/HTLV III, in macaques immunized with the recombinant viruses. In addition to their probable role in the differentiation of B cells to produce antibodies to LAV/HTLV III envelope antigens, these IL-2 producing T cells may be involved in differentiation and/or expansion of effector cells, such as cytotoxic T lymphocytes or natural killer cells that can kill virus infected cells.

Taken together, the results shown in Tables I, II, and III indicate that immunization of macaques with recombinant vaccinia viruses that express the LAV/HTLV III envelope glycoproteins, results in T cell-mediated immune responses to LAV/HTLV III, generating T cells that can be activated in vitro, as shown by (a) proliferation of the T cells in response to stimulation with LAV/HTLV III, and (b) production of IL-2 by the T cells in response to stimulation with LAV/HTLV III. Since the envelope antigens are the only LAV/HTLV III antigens encoded by the recombinant vaccinia virus used for immunization, it is apparent that, in this specific embodiment, the T cells which proliferate and produce IL-2 following stimulation with LAV/HTLV III, recognize the LAV/HTLV III envelope antigen(s). It is also evident that the envelope antigens expressed by the recombinant virus and those expressed by LAV/HTLV III, are immunologically cross-reactive.

EXAMPLE: IN VITRO ACTIVATION OF CHIMPANZEE T CELLS SPECIFIC TO LAV/HTLV III.

The experiment described infra shows that PBL from v-env5NY vaccinated chimpanzees proliferate in response to stimulation with LAV/HTLV III or with LAV/HTLV III envelope glycoproteins in vitro.

PBL were isolated from heparinized blood by Ficoll-hypaque centrifugation four weeks after a second intradermal inoculation with v-env5NY or with a recombinant vaccinia virus expressing herpes simplex virus type I glycoprotein (vHSVgD1). The PBL were seeded at $1 \times 10^5$ cells/well in 96-well plates, in RPMI 1640 medium supplemented with 10% heat-inactivated normal human serum and penicillin/streptomycin. Then non-disrupted LAV/HTLV III (5 ug/ml), LAV/HTLV III envelope glycoproteins (1 ug/ml) isolated by lentil lectin chromatography from purified LAV/HTLV III, UV inactivated HSV-1 ($1 \times 10^5$ pfu/ml prior to UV inactivation) or UV inactivated v-env5NY ($1 \times 10^6$ pfu/ml prior to UV inactivation) was added to replicate wells. Five days later, $^3$H-thymidine incorporation into the cells was determined by liquid scintillation counting. The results are shown in Table IV.

TABLE IV
PROLIFERATIVE RESPONSES OF PBL FROM CHIMPANZEES IMMUNIZED WITH RECOMBINANT VACCINIA VIRUSES

| Immuni-zation | cpm $^3$H-Thymidine Incorporated After Stimulation With: | | | | |
|---|---|---|---|---|---|
| | No Antigen | Env (1 ug/ml) | Lav/HTLVIII (5 ug/ml) | uv-inactivated HSV-1 | uv-inactivated v-env5NY |
| Post Boost* v-env5NY | | | | | |
| 124 | 3,626 | 54,685 | 50,197 | 5,967 | 105,840 |
| 149 | 2,257 | 21,178 | 8,938 | 3,347 | 137,857 |
| V-HSVgD1 | | | | | |
| 134 | 4,817 | 3,652 | 4,428 | 79,455 | 92,192 |
| Post 1*** v-env5NY | | | | | |
| 216 | 170 | 13,702 | 18,772 | 1,965 | 39,950 |
| 72 | 1,552 | 25,245 | 34,252 | 2,162 | 82,167 |
| V-HSVgD1 | | | | | |
| 64 | 5,300 | 7,300 | 7,560 | 6,990 | 125,372 |

*4 weeks post boost; 124, 149 and 134 refer to Chimpanzee identification numbers;
**8 weeks post primary immunization; 216, 72, 64 refer to Chimpanzee identification numbers.

PBL from all of the chimpanzees incorporated high levels of $^3$H-thymidine incorporation following stimulation with v-env5NY (due to T cell response to vaccinia virus). As shown in Table IV, PBL from all the chimpanzees immunized with v-env5NY showed significant proliferative responses to LAV/HTLV III and LAV/HTLV III envelope glycoproteins (env), in contrast to PBL from the v-HSVgD1-immunized chimpanzees (No. 134 and No. 64).

EXAMPLE: IN VITRO GENERATION OF CHIMPANZEE T CELL CLONES WITH PROLIFERATIVE AND CYTOTOXIC ACTIVITIES DIRECTED AGAINST LAV/HTLV III ENVELOPE ANTIGENS

The experiment described infra shows that T cell clones that proliferate following stimulation with v-env5 but not parental vaccinia virus and that lyse $^{51}$Cr-labeled autologous target cells infected with v-env5 but not parental vaccinia virus, can be generated in vitro from PBL of a chimpanzee immunized with v-env5. The PBL were stimulated twice at weekly intervals with purified AIDS virus envelope antigens (env, 1 ug/ml). Three days later the stimulated cells were cloned by limiting dilution in wells of 96 well plates to which were added $5 \times 10^4$ x-irradiated (2500R) autologous PBL (and UV-inactivation) in complete medium containing 10% delectinated IL-2 (Cellular Products, Buffalo, N.Y.). The clones were expanded by weekly feeding with v-env5 and x-irradiated PBL in IL-2 containing medium. To test for proliferative response to v-env5 and vaccinia virus, the cloned T cells were washed free of IL-2 and $1 \times 10^4$ cloned T cells were placed in replicate wells containing $5 \times 10^4$ x-irradiated autologous PBL and v-env5 or vaccinia virus ($1 \times 10^6$ pfu/ml prior to UV-inactivation) in IL-2 free medium. Three days later, $^3$H-thymidine was added to the wells and $^3$H-thymidine incorporated during 6 hours was determined by liquid scintillation counting. The results in Table V show that all 4 clones proliferated in response to v-env5, but not to parental vaccinia virus.

The cloned cells were also tested for their ability to lyse $^{51}$Cr-labeled autologous lymphoblastoid target cells infected with v-env5, vaccinia virus, or no virus in a 6 hour $^{51}$Cr release assay using a cloned effector cells:-target cell ratio of 25:1. The results are shown in Table V. The cloned cells lysed v-env5 infected cells but not parental vaccinia or uninfected cells thus demonstrating their specificity for AIDS virus envelope antigen(s).

TABLE V
PROLIFERATIVE AND CYTOTOXIC ACTIVITIES OF CLONED T CELLS FROM venv5 IMMUNIZED CHIMPANZEE #124

| Clone # | cpm $^3$H-Thymidine Incorporation After Stimulation With: | | |
|---|---|---|---|
| | No Antigen | v-env5 | Vaccinia |
| 1 | 5,317 | 33,907 | 8,272 |
| 2 | 4,997 | 15,225 | 6,342 |
| 3 | 1,090 | 9,080 | 2,910 |
| 4 | 4,607 | 13,050 | 5,392 |

| Clone # | % $^{51}$Cr Release From Target Cells Infected With: | | |
|---|---|---|---|
| | No Virus | v-env5 | Vaccinia |
| 1 | −2.4 | 20.2 | −0.1 |
| 2 | −0.7 | 7.0 | −1.3 |
| 3 | −0.0 | 11.0 | 1.0 |
| 4 | −0.1 | 23.5 | −3.2 |

EXAMPLE: IN VITRO ACTIVATION OF HUMAN T CELLS WITH V-ENV5

The experiment described infra shows that PBL of AIDS virus seropositive individuals proliferate in response to stimulation with v-env5 in vitro. PBL were isolated by Ficoll-Hypaque centrifugation, and resuspended in RPMI 1640 medium containing 10% heat-inactivated pooled normal human serum. Then 0.1 ml PBL ($1 \times 10^5$ cells) was added to each of four replicate wells followed by the addition of 0.1 ml medium (no antigen), 0.1 ml ultraviolet (UV)-inactivated v-env5 ($10^6$ pfu/ml prior to UV-inactivation) or $1 \times 10^5$ X-irradiated (2500R) allogeneic PBL. Six days later, $^3$H-thymidine ($^3$H-TdR) was added to the wells (0.5 uCi/well), and six hours later the cells were harvested by a multi-well harvesting apparatus. $^3$H-TdR incorporation was determined by liquid scintillation counting. The stimulation index (S.I.) was calculated by dividing the cpm $^3$H-TdR incorporated into stimulated cells by the cpm incorporated into non-stimulated cells. The results are shown in Table VI.

TABLE VI

VACCINIA-ENV RECOMBINANT VIRUS V-ENV5 INDUCED PROLIFERATIVE RESPONSES OF T CELLS FROM AIDS VIRUS SEROPOSITIVE AND SERONEGATIVE INDIVIDUALS

| | | Lymphocytes Stimulated With: | | | | |
|---|---|---|---|---|---|---|
| In-divi-dual | Sero + or Sero − | No Antigen cpm* | V-env5 cpm* | V-env5 SI** | Allogeneic Cells cpm* | Allogeneic Cells SI** |
| Exp. 1333 | + | 3,982 | 11,140 | 2.8 | 28,067 | 7.1 |
| 1   Y-1 | + | 2,290 | 12,772 | 5.6 | 32,382 | 14.1 |
|     1 | − | 2,790 | 38,317 | 13.7 | 29,827 | 10.7 |
|     2 | − | 1,487 | 73,392 | 49.4 | 56,380 | 37.9 |
| Exp. Y-1 | + | 3,487 | 12,505 | 3.6 | 23,225 | 6.6 |
| 2   AB | + | 1,470 | 5,720 | 3.9 | 4,470 | 3.0 |
| Exp. RE | + | 140 | 710 | 5.1 | 61,162 | 437.9 |
| 3   BM | − | 3,925 | 48,140 | 12.3 | 28,092 | 7.2 |
|     2331 | + | 1,847 | 36,447 | 19.8 | 36,475 | 19.8 |

*cpm $^3$H-thymidine incorporated
**Stimulation Index

As seen in Table V, the PBL of both seropositive and seronegative donors showed proliferation in response to v-env5. In general, PBL from seropositive donors showed a lower response than seronegative donors. However, PBL of seropositive donors showed a significant response, and the activated T cells can be expanded in IL-2-containing cell culture.

DEPOSIT OF MICROORGANISMS

The following recombinant viruses have been deposited with the American Type Culture Collection, Rockville, Md., and have been assigned the listed accession numbers:

| Recombinant Virus | Accession Number |
|---|---|
| v-env2 | ATCC VR 2114 |
| v-env5 | ATCC VR 2113 |
| v-env7 | ATCC VR 2148 |
| v-env5NY | ATCC VR 2149 |
| v-gag1NY | ATCC VR 2150 |
| Ac-gag1 | ATCC VR 2147 |
| Ac-env5 | ATCC VR 2151 |

The present invention is not to be limited in scope by the recombinant viruses deposited since the deposited embodiment is intended as a single illustration of one aspect of the invention and any recombinants which are functionally equivalent can be used within the scope of this invention. Indeed, various modifications of the invention in addition to those shown and described herein will become apparent to those skilled in the art from the foregoing description. Such modifications are intended to fall within the scope of the appended claims.

What is claimed is:

1. A method for activating T-lymphocytes specific for the AIDS virus in vitro, comprising exposing lymphocytes, derived from an individual who was previously exposed to an AIDS-virus envelope protein or fragment thereof, to the AIDS-virus envelope protein or fragment thereof in vitro, so that T-lymphocytes specific for the AIDS-virus are activated.

2. The method according to claim 1 further comprising the steps of selecting activated T-lymphocytes by either of the following assays:
   (i) a cytotoxicity assay in which the activated T-lymphocytes are incubated with the persons's radiolabelled target cells infected with AIDS virus, the release of radiolabel being an indication of lysis of the infected target cells; or
   (ii) a stimulation assay which measures the ability of the activated T-lymphocytes to proliferate and/or produce a lymphokine in response to stimulation with an epitope of the AIDS virus in vitro.

3. The method according to claim 1 or 42 in which T-Lymphocytes are activated in vitro by exposure to a recombinant microorganism that expresses an AIDS-virus envelope protein or fragment thereof.

4. The method according to claim 3 in which the recombinant microorganism comprises a recombinant virus.

5. The method according to claim 4 in which the recombinant virus comprises an animal virus.

6. The method according to claim 5 in which the animal virus comprises a vaccinia virus.

7. The method according to claim 4 in which the recombinant virus comprises an insect virus.

8. The method according to claim 7 in which the insect virus comprises a baculovirus.

9. The method according to claim 4 in which the T-lymphocytes are activated by exposure to v-env5 as deposited with the ATCC and assigned accession number ATCC VR2113.

10. The method according to claim 4 in which the recombinant virus is v-env5NY as deposited with the ATCC and assigned accession number ATCC VR2149.

11. The method according to claim 4 in which the recombinant virus is Ac-env5 as deposited with the ATCC and assigned accession number ATCC VR2151.

12. The method according to claim 1 or 2 in which the person was previously exposed to the AIDS virus.

13. The method according to claim 1 or 2 in which the person was previously exposed to the AIDS envelope protein or fragments thereof.

14. The method according to claim 1 or 2 in which the person was previously exposed to a recombinant virus that expresses the AIDS envelope protein or fragments thereof.

15. The method according to claim 1 or 2 in which the person was previously exposed to V-env5 as deposited with the ATCC and assigned accession number ATCC VR2113.

16. The method according to claim 1 or 2 in which the person was previously exposed to v-env5NY as deposited with the ATCC and assigned accession number ATCC VR2149.

17. The method according to claim 1 or 2 in which the person was previously exposed to AC-env5 as deposited with the ATCC and assigned accession number ATCC Vr2151.

* * * * *